United States Patent [19]
Kurita

[11] Patent Number: 5,216,624
[45] Date of Patent: Jun. 1, 1993

[54] AUTOMATED FOSSIL-REFLECTANCE MEASUREMENT APPARATUS AND METHODS

[76] Inventor: Hiroshi Kurita, 7-11-306, Takatsu-Danchi, Yachiyo-shi, Chiba-Ken, Japan

[21] Appl. No.: 824,416

[22] Filed: Jan. 23, 1992

Related U.S. Application Data

[63] Continuation-in-part of Ser. No. 540,144, Jun. 19, 1990, abandoned.

[30] Foreign Application Priority Data

Jul. 11, 1989 [JP] Japan .................................. 1-177100

[51] Int. Cl.$^5$ ........................ G06F 15/46; G06F 15/20
[52] U.S. Cl. .................................... 364/556; 364/497; 364/550; 358/107
[58] Field of Search ............... 364/506, 556, 525, 550, 364/497, 499; 356/432, 408; 250/358.1, 360.1; 358/106, 107, 903

[56] References Cited

U.S. PATENT DOCUMENTS

| | | | |
|---|---|---|---|
| 4,491,411 | 11/1985 | Goldstein | 356/30 |
| 4,591,718 | 5/1986 | Amer | 250/339 |
| 4,617,682 | 10/1986 | Mori et al. | 358/107 X |
| 4,682,158 | 7/1987 | Ito et al. | 364/185 X |
| 4,815,014 | 3/1989 | Lipner et al. | 364/550 |
| 4,852,182 | 7/1989 | Herbin et al. | 382/1 |
| 4,882,763 | 11/1989 | Buchan et al. | 382/1 |

OTHER PUBLICATIONS

"Quantimet 520: Image Analysis System"; Cambridge Instruments Ltd.; Dec. 1986.
"Discover the Power of the ACAS 470"; Meridian Instruments, Inc.; 1986.

Primary Examiner—Kevin J. Teska
Attorney, Agent, or Firm—Joseph C. Mason, Jr.; Ronald E. Smith

[57] ABSTRACT

A computer operated, automated microscopic apparatus (1) has an automated microscope (2) that is computer operated, a computerized sample-input mechanism (3–18 and 34–42), a computerized sample-processing mechanism (19–33) and methods for automatic operation.

13 Claims, 10 Drawing Sheets

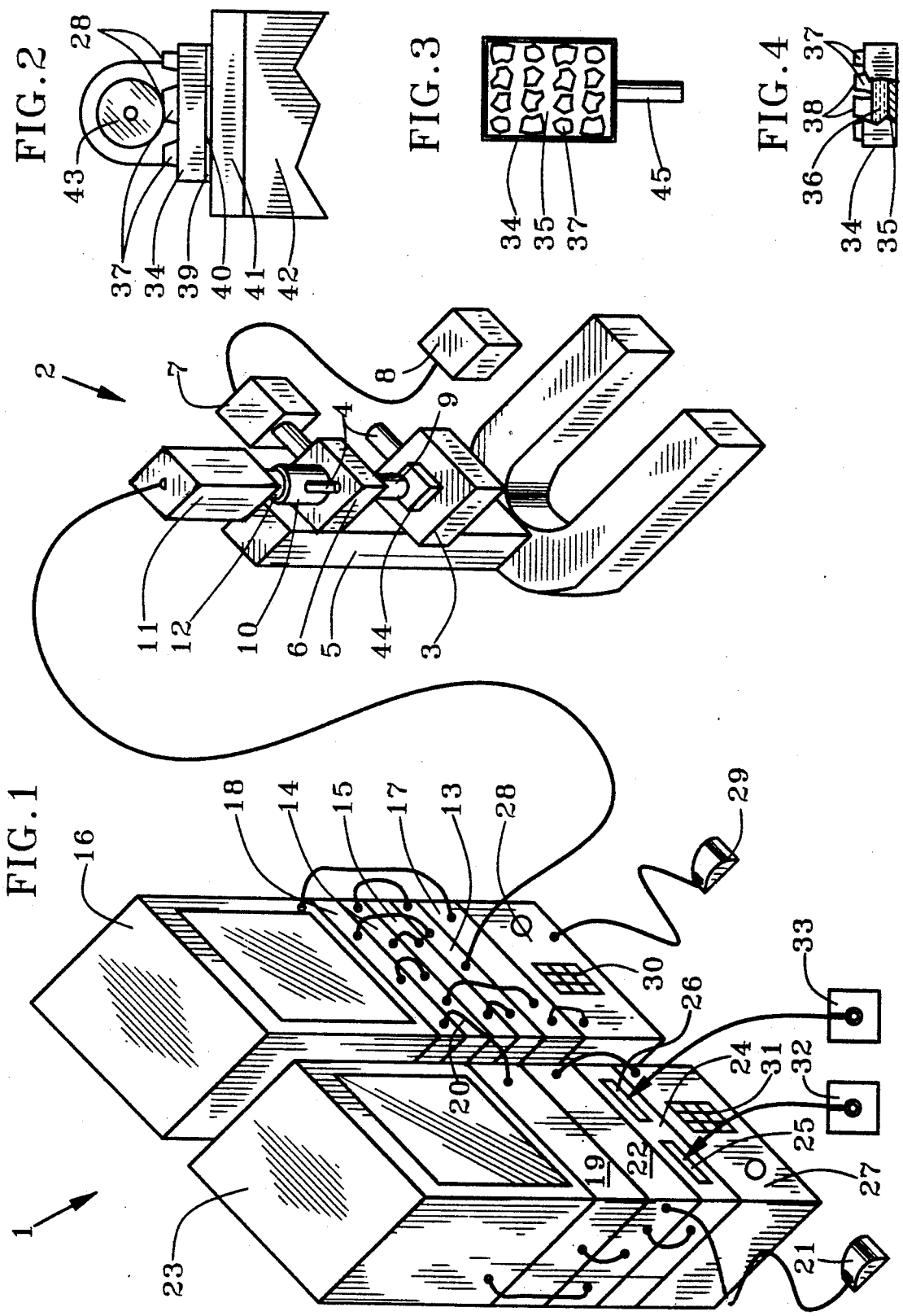

AUTOMATED FOSSIL-REFLECTANCE MEASUREMENT APPARATUS AND METHODS

This is a continuation-in-part of U.S. patent application No. 540,144, filed Jun. 19, 1990 by the same inventor, H. Kurita, now abandoned.

BACKGROUND OF THE INVENTION

1. Field of the Invention

This invention relates to measuring reflectance of fossil substances such as vitrinite macerels in coal and oil-shale kerogen to determine their geological age, carbon content, fuel energy per volume and suitability for particular fuel uses. Favorableness of geological conditions for oil and gas as well as their probable composition in areas of deposits of coal and oil shale is indicated also by measurement of vitrinite and other fossil reflectance. In particular, this invention makes quick, reliable and convenient measurement of reflectance of samples of sedimentary fossil rock achievable by non-technical personnel.

2. Description of Related Art

Instrumentation suitable for accurate measurement of reflectance of vitrinite by skilled laboratory personnel and technical specialists is available in the prior art. Examples are described in "QUANTIMET 520" by Cambridge Instruments Co., "ACAS 470" by Meridian Co., and "BIOVISION" by Perceptics Co. Instrumentation described in all three of these references is for generalized use that requires specialists to operate. Neither the physical arrangement, structure, capability nor methods of using known instrumentation are suitable for operation by a generalist, by specialists skilled in other technology or by non-technical personnel. Japanese Patent Number 58-22940 likewise teaches very appropriate instrumentation for reflectance analysis of coal but requires operation by a specialist rather than by unskilled personnel. U.S. Pat. No. 4,617,682 by Mori et al describes instrumentation structured in some ways similar to parts of this invention but without modifications and working relationships of parts for use by unskilled personnel. It is structured to test for uniformity of sample materials. It would require technically-skilled personnel, rather than non-technical employees, to use it for measuring reflectance of vitrinite, kerogen and other fossil substances. Further, it would require much time and would not be sufficiently reliable nor economical for such use even by those skilled in the art to which it appertains.

Other devices less suitable yet for reflectance analysis of hard fossil deposits by non-technical personnel are described in U.S. Pat. No. 4,591,718 by Amer and U.S. Pat. No. 4,491,411 by Goldstein. The Amer patent describes a device for infrared spectroscopy. The Goldstein patent is for measuring uranium content in ores. Neither could be used effectively nor economically for measuring reflectance of vitrinite by either skilled or unskilled personnel.

Measuring reflectances of fossils is vital to modern civilization for a variety of reasons related to paleontology of fossil fuel. Algae and insects developed earlier in aeons of geological time than larger forms of plant and animal life. They were not as abundant and concentrated relative to conditions around them because there was not a habitat of other forms of life that were larger and more massive for deposit of their remains in formation of fossil materials. They are not as dense or concentrated in proportion to inorganic materials around them, even though aged longer. Consequently, there is much rock among their remains. In combination with inorganic rock, their remains form what is known as oil shale. Their organic fossil remains are known as kerogen. Kerosene was one of the first commercial products produced from their remains. Petroleum products can be obtained from heating the oil shale because of its older and more "coalified" condition with more concentrated forms of carbon. Even though old and high in carbon content, however, its reflectance is low because the algae and insects from which it was formed are not as dense as life forms that developed later. Reflectance of fossil results from carbon density. Consequently, kerogen reflectance is relatively low and difficult to measure.

Fossil remains from larger and more dense plant and animal life formed higher densities of fossil carbon materials. As they aged, their remains became liquid and seeped to lower levels as present petroleum deposits if the geological conditions of overburden were sufficiently conducive to such processing by nature. Fossil remains of the same age or of less age that were in less favorable conditions for formations of liquids formed coal or coal tars, depending on the geological conditions. Thus the nature of coal and kerogen in sedimentary conditions for fossil development can be indicative of the nature of petroleum and its likelihood of existence.

As coal ages under conditions favorable for development of coal, rather than petroleum, its volatile products diminish and its density of carbon increases. Carbon is the fundamental constituent of fossil fuel. Thus its density determines BTU's per pound of fossil fuel. BTU's per pound of coal, for instance, can range from 14,000 for grades of anthracite coal to 9,000 for grades of bituminous coal. Peat from which they develop has approximately 5,000. In addition to density of latent heat, there is also the ability of coal to swell in coke production processes for yielding various grades of coke for smelting different types of ores and scrap materials.

A fossil carbon compound known as vitrinite has a reflectance of light in proportion to density and, therefore, a reflectance which indicates the age and development of fossil fuel, particularly coal. Other types of carbon deposits known as exinites and inertinites have less reflectance. Vitrinite occurs in concentrations known further as vitrinite macerals. Between vitrinite macerals, there are less dense carbon materials and combinations of organic and inorganic materials. Measuring reflectances of vitrinite, therefore, requires measurement of not only vitrinite macerals, but also the less dense and less reflective materials between the vitrinite macerals. Some of the materials between the vitrinite macerals is resinous, less reflective and causes "noise" in electronic systems of measurement. Some types of plant and animal remains in fossil materials have more dense carbon than others.

Before the advent of measuring reflectance of vitrinite macerals and before present paleontological methods for predicting existence of oil and gas, there was a wide variety of methods for analyzing coal. All were manual and macroscopic rather than microscopic. Observable physical layering, measuring proportions of volatile matter and measuring pore space were included. It was difficult and subject to inaccuracy due to subjectivity.

Now, by measuring reflectance, analyzing fossil materials is much more accurate. But it is still fraught with difficulties, inaccuracies and high costs resulting from the nature of present equipment and methods for measuring reflectance. Exorbitant time of highly-skilled individuals is required. Fatigue causes inaccuracies. Precise standardization is lacking. The equipment is bulky and difficult to transport to areas of need.

It was to overcome difficulties and limitations of present equipment and methods for measuring reflectances of fossil material and to increase the scope of measurable fossil materials that inspired this invention.

SUMMARY OF THE INVENTION

One objective of this invention is to provide a computer-operated, automated microscopic apparatus and methods for analyzing quality of coal by measuring reflectance of vitrinite macerals which indicate carbon content due to geological aging and coalification of coal.

Another objective of this invention is to provide a computer-operated, automated microscopic apparatus and methods for analyzing suitability of coal for production of various grades of coke for different industrial applications.

Another objective of this invention is to provide a computer-operated, automated microscopic apparatus and methods for measuring relatively low reflectance of kerogen to determine suitability of oil shale for production of petroleum and related products.

Another objective of this invention is to provide a computer-operated, automated microscopic apparatus and methods for measuring reflectance of kerogen, exinites and inertinites as well as vitrinite macerals in fossil materials to indicate favorableness of geological conditions and likely composition of oil and gas in areas where they are found.

Another objective of this invention is to provide a computer-operated, automated microscopic apparatus and methods which can be operated by individuals not skilled in the use of laboratory equipment and analysis.

Another objective of this invention is to provide a computer-operated, automated microscopic apparatus and methods which eliminate need for users to check personally vitrinite particles in a sample to permit automatic measurement.

Another objective of this invention is to provide a computer-operated, automated microscopic apparatus and methods which do not require professional knowledge of coal structures and various types of fossils to enable utilization effectively and easily.

Another objective of this invention is to provide a computer-operated, automated microscopic apparatus and methods which permit users to maintain constant criterion for analysis of coal structures and various types of fossils.

Another objective of this invention is to provide a computer-operated, automated microscopic apparatus and methods which eliminates personal error due to fatigue and distraction in the previously arduous and time-consuming task of measuring reflectances for analyzing coal structures and various types of fossils.

Another objective of this invention is to provide a computer-operated, automated microscopic apparatus and methods which permit more samples per unit of time to be processed in comparison to what is possible with conventional equipment and methods in order to increase economic efficiency of measuring reflectances to analyze coal structures and various types of fossils.

Yet another objective of this invention is to provide a computer-operated, automated microscopic apparatus and methods which eliminate need for users to observe dark fields of view under a microscope for repeating tedious, complicated, time-consuming, labor-intensive, tiring and mentally-exhausting operations required previously for measuring reflectances to analyze coal structures and various types of fossils with present equipment and methods.

This invention accomplishes the above and other objectives with a computer-operated, automated microscopic apparatus and methods having an automated microscope that is computer-operated, a computerized sample-input mechanism, a computerized sample-processing mechanism and methods for automatic operation.

BRIEF DESCRIPTION OF THE DRAWINGS

This invention is described by appended claims in relation to description of a preferred embodiment with reference to the following drawings wherein:

FIG. 1 is a perspective view of the apparatus.

FIG. 2 is a sectional view of a surface grinder in relation to a sample tray with samples glued in it.

FIG. 3 is a top view of a sample tray containing samples.

FIG. 4 is a cutaway end view of a sample tray containing samples and adhesive material.

DESCRIPTION OF PREFERRED EMBODIMENT

Figure 5:
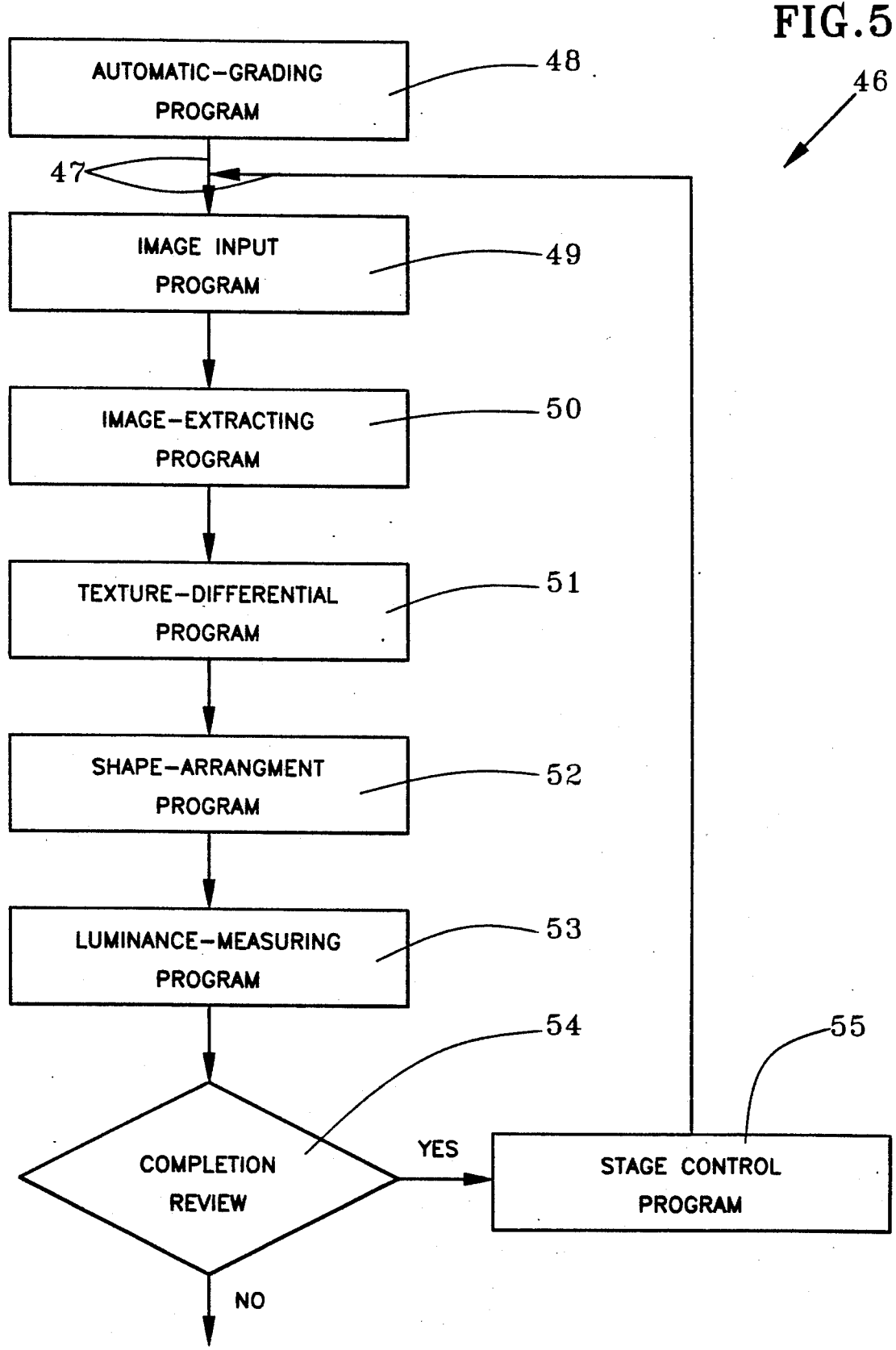
FIG. 5 is a flow chart of a sequential control program.

Reference is made first to FIG. An automated fossil-reflectance measurement apparatus 1 is provided with an automated microscope 2. The automated microscope 2 has a sample platform 3 that can be positioned selectively or otherwise operated in X-Y coordinates by a step motor 4. Ordinarily a platform on which a sample is positioned for viewing on a microscope is referred to as a stage. Stages, however, connote a fixed position. In the case of an automated microscope, such a stage is moveable in coordinates for automatic repositioning of a sample or of a plurality of samples. Hence its designation as a sample platform 3. The step motor 4 can be either linear or rotational and there can be one geared to move the platform 3 in different directions or a plurality of step motors for moving the platform 3 in different directions. The sample platform 3 can be attached to a fixed support 5. An epi-prism device 6 having a light source 7 can be positionable a select distance vertically from the sample platform 3 and can be attachable to the fixed support 5. The light source can have a control means 8 for automatic light adjustment in relation to requirements of automated microscopic operations. A lens 9 is extendible vertically in relationship to a lens barrel 10 above the epi-prism device 6 in well-known working relationships of these particular components. An image-pickup television camera 11 is positionable above the lens barrel 10 where it can be attachable concentrically and adjustable to the lens barrel 10 by a camera attachment arm 12. Focussing with the lens barrel 10 also can be controlled remotely by a separate step motor 4.

Referring further to FIG. 1, the image-pickup television camera 11 and all electrically-operated components such as step motors and control means downstream electrically from the camera 11 are connectable electrically to a digital converter 13 which is connectable according to well-known methods and components to an image-operating processor 14. The image-operating processor 14 is connectable to an image memory 15 and to a television monitor 16 by way of a television interface 17. A two-way communication monitor interface 18 also is connectable to the image-operating processor 14.

Referring further to FIG. 1, a two-way communication processor interface 19 is connectable to the monitor interface 18 through a bidirectional-communication cable 20. A computer mouse 21 is connectable in operative relationship to a process controller 22 to which the processor interface 19 also is connectable. A processor display unit 23 is connectable to the process controller for displaying data being processed. A storage-medium input-output device 24 also is connectable to the process controller 22. Control-program bay and operating means 25 and recording-program bay and operating means 26 are positionable in the storage-medium input-output device 24. Referring further to FIG. 1, processing components 19–26 can be provided with an optional process control means 27. Likewise, image-input, microscope and television components 1–18 can be provided with an image-input control means 28. The process control means 27 and image-input control means 28 can be provided with a computer keyboard or various knobs for each group of components or such other control mechanisms for computer equipment as are well-known in the art to which they appertain. An input computer mouse 29 also may be provided. Control mechanisms illustrated for example are television computer keyboard 30 and processing computer keyboard 31. Positionable respectively into bays 25 and 26 are control-program computer disk 32 and recording-program computer disk 33.

Referring now to FIGS. 2–4, a sample tray 34 is provided with sample bay 35 into which hardenable adhesive 36 can be placed for holding samples 37 rigidly while top surfaces 38 of the samples 37 are being ground to uniform height. A magnetic plate 39 can be provided on a bottom edge 40 of the sample tray 34 for positioning the sample tray 34 on a grinding bed 41 of a surface-grinding machine 42 for surface preparation and on the sample platform 3 for analysis. Typically, samples 37 are soft enough to be ground easily by grinding wheels 43 that are relatively inexpensive. Either a single sample 44 independent of sample tray 34 or a plurality of samples 37 in the tray 34 can be positioned on platform 3. However, when a tray 34 of samples 37 is used, much time can be saved and a plurality of samples can be handled by a tray handle 45 conveniently for systematic storage.

Referring further to FIGS. 2–4, use of surface grinder 42 to obtain flat surfaces 38 enables rapid repositioning or changing of coordinates of one or more samples 37 or 44. This is highly significant to rapid and reliable automatic operation of the microscopic portion of this invention. Further yet, grinding in this manner decreases extraneous factors on surfaces 38 that could obstruct reflectance measurement.

Referring further yet to FIGS. 2–4, the trays 34 can be variously sized and shaped for different types and sizes of samples 44 and 37. Samples in a size range of several millimeter cubes would require a tray 34 with a bay 35 only a few millimeters deep. Alternatively, a false-bottom platform can be positioned in the bay 35 or in parts of it to raise short samples 37 to the approximate height of larger samples 37 for uniform surface grinding. Alternatively also, the sample platform 3 can be provided with a vertical Z axis. The preferred method for adjustment to heights of samples 37 is positioning various block platforms on the adhesive material 36 and then putting adhesive material on top of the blocks to hold the samples 37 rigidly. Blocks need not be uniform in height and need not position tops 38 of samples 37 accurately because accuracy of height can be provided by grinding with the grinder 42.

Construction and functional characteristics of these parts is known well in prior art. But this particular working relationship of parts for automating them to be operated by individuals not skilled in laboratory equipment and techniques is considered to be novel and utilitarian. It is not considered to be obvious to one skilled in the art to which it appertains by evidence of its novelty when so much effort has been applied to development of related components previously. This is a dedicated machine. Dedicated machines can be made to require less specialization of individuals for their operation. Conversely, more generalized equipment can require more specialized and highly-trained individuals for their operation. Dedicated machinery replaces high-priced human skills with this invention. Further, the time required for operation of this dedicated equipment by unskilled personnel is less than required for operation of non-dedicated, generalized equipment that exists in the prior art.

To teach and to facilitate operation of this dedicated machinery by individuals relatively unskilled in laboratory equipment and methods, operational instructions are provided and described in relatively general method claims. Supportive of these general method claims are more detailed method claims describing programs and method steps which are performed in accordance with the operational instructions. Well-known programming methods and techniques are employed, but the working relationship of program elements, their sequence and formation for effective operation are believed to be novel, the same as for the working relationship of apparatus hardware elements. All are described in a manner that this invention can be practiced by those skilled in the art to which it appertains.

Referring to FIG. 5, a sequential control program 46 with directional arrows 47 has a calibration curve auto-preparing and generally automatic-grading program 48, an image input program 49, an image-extracting program 50, a texture-differential program 51, a shape-arrangement program 52, a luminance-measuring program 53, a completion review 54 and an objective stage control program 55. Operational sequence of the programs is in accordance with the arrows 47 between blocks representing each program and program component. Each of these programs are steps in programmed method 46.

Figure 6:
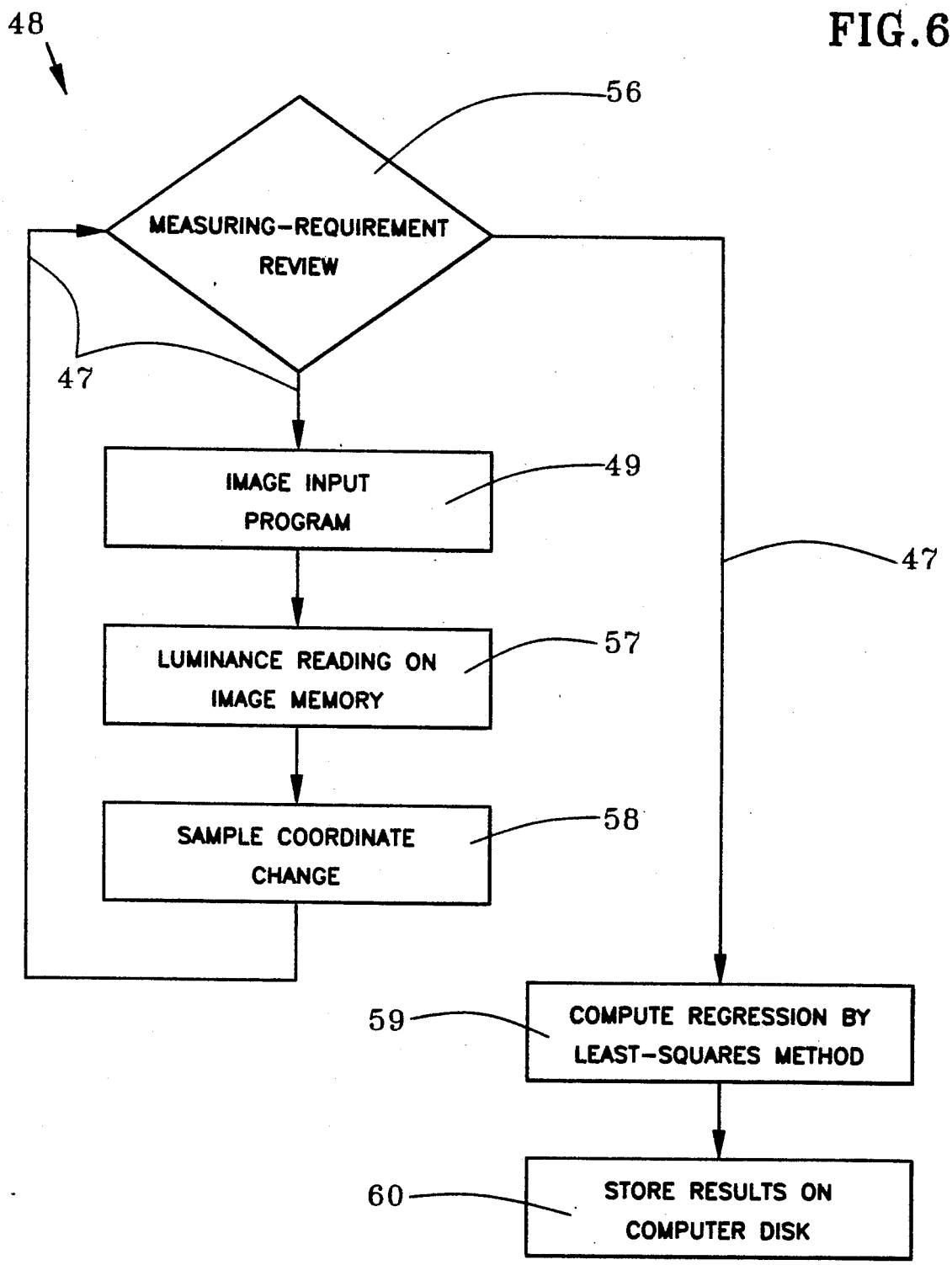
FIG. 6 is a flow chart of an automatic grading program.

Referring to FIG. 6, the calibration curve auto-preparing program 48 is comprised further of a measuring-requirement review and calibration step 56, an image input program 49, a luminance reading on image memory 57, and a sample coordinate change 58 in the sequence indicated for measuring reflectance of particular fossil materials. For those materials not requiring steps 49, 57 and 58, and for those materials which have been processed through steps 49, 57 and 58, step 59 compute regression by least-squares method and step 60 store results on computer disk are taken.

Figure 7:
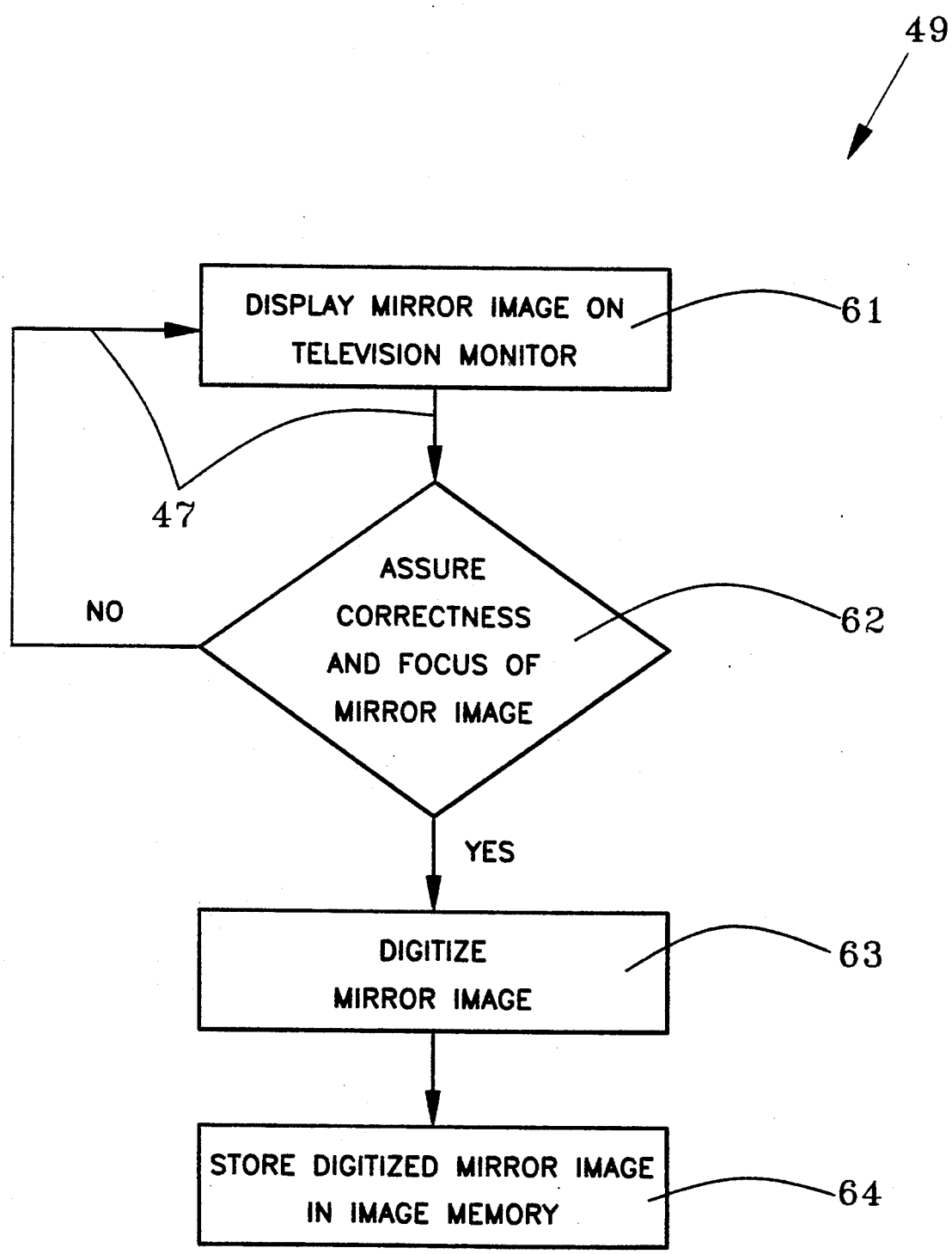
FIG. 7 is a flow chart of an image input program.

Referring to FIG. 7, the image input program 49 is comprised further of step 61 display mirror image on television monitor and step 62 assure correctness and focus of mirror image, step 63 digitize mirror image and step 64 store digitized mirror image in image memory. Each step proceeds in the sequential order indicated by arrows 47 between blocks representing each step and in accordance with yes and no decisions indicated.

Figure 8:
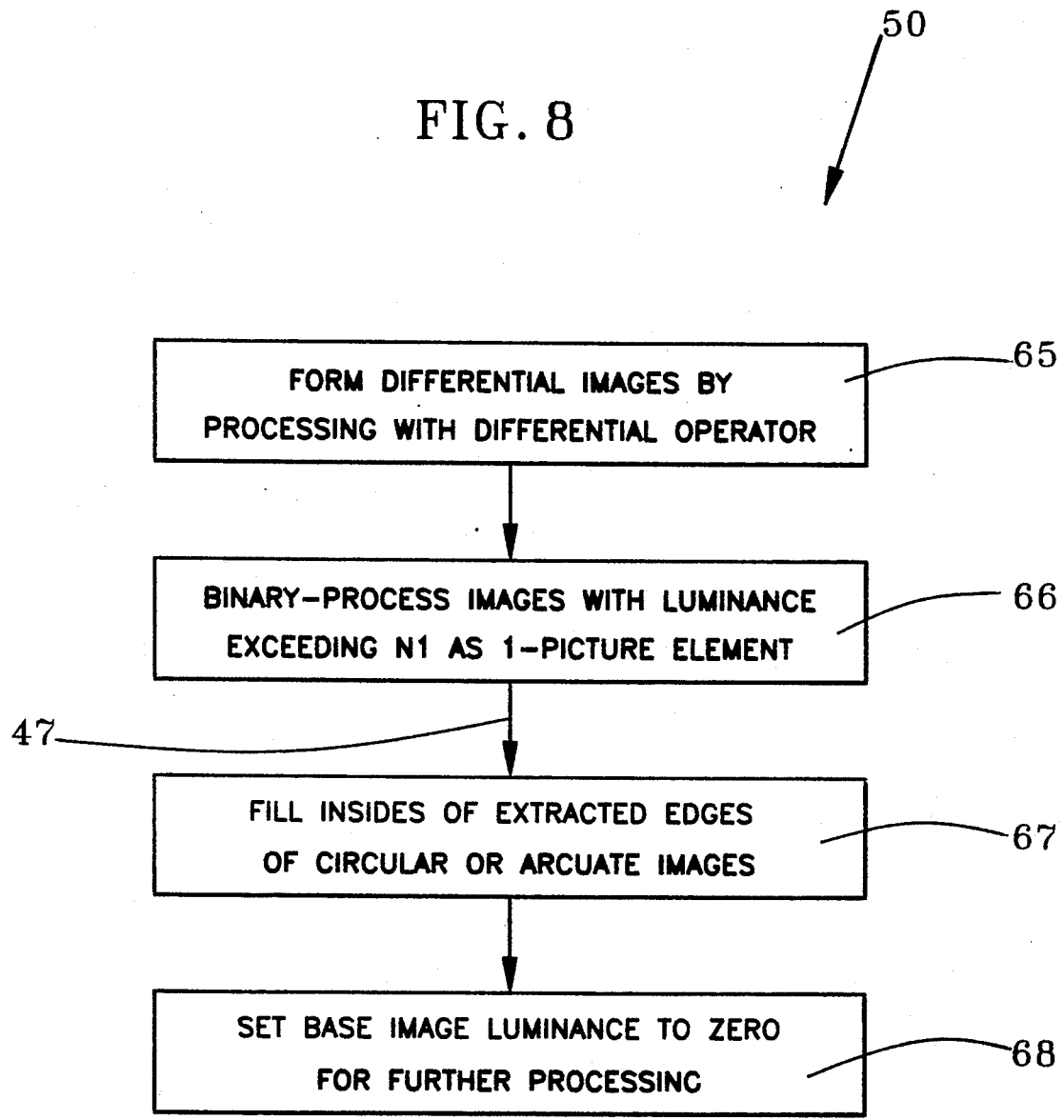
FIG. 8 is a flow chart of an image extracting program.

Referring to FIG. 8, the image-extracting program 50 is comprised further of step 65 differential image formation with differential operator, step 66 binary process of N1 luminance images as 1-picture element, step 67 fill insides of extracted edges, and step 68 set base image luminance to zero for further processing.

Figure 9:
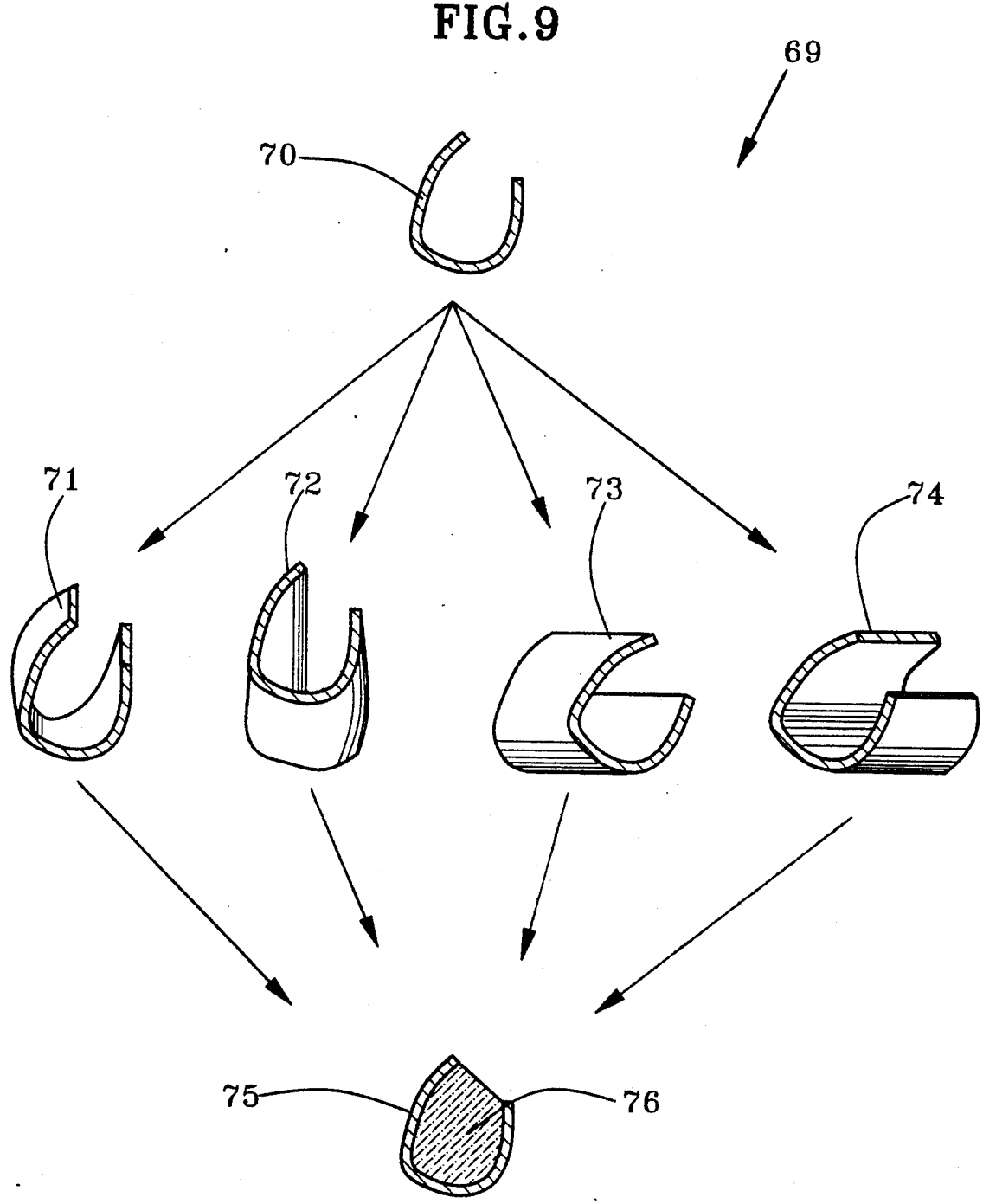
FIG. 9 is a diagram of an image-filling process.

Referring to FIG. 9, a filling process 69 is made as follows. A sample image 70 for image filling is diffused in four directions separately from an up side 71, a down side 72, a left side 73 and a right side 74. A filled image 75 is illustrated with filled portion 76.

Figure 10:
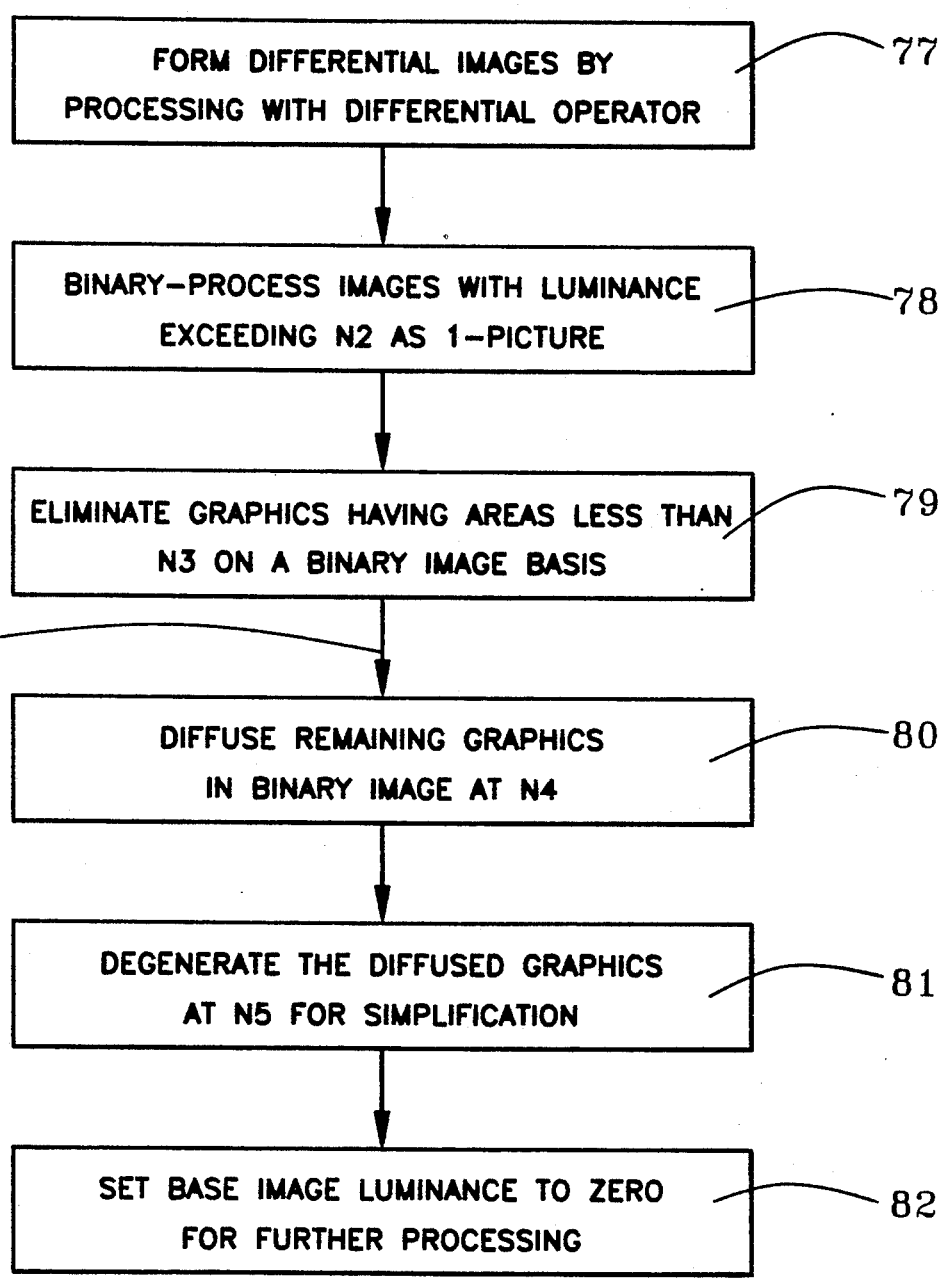
FIG. 10 is a flow chart of a fine-texture-differential program.

Referring to FIG. 10, the fine-texture differential program 51 is comprised further of step 77 form differential images by processing with differential operator, step 78 binary-process images with luminance exceeding N2 as 1-picture, step 79 eliminate graphics having areas less than N3 on a binary image basis, step 80 diffuse remaining graphics in binary image at N4, step 81 degenerate the diffused graphics at N5 for simplification, and step 82 set base image luminance to zero for further processing.

Figure 11:
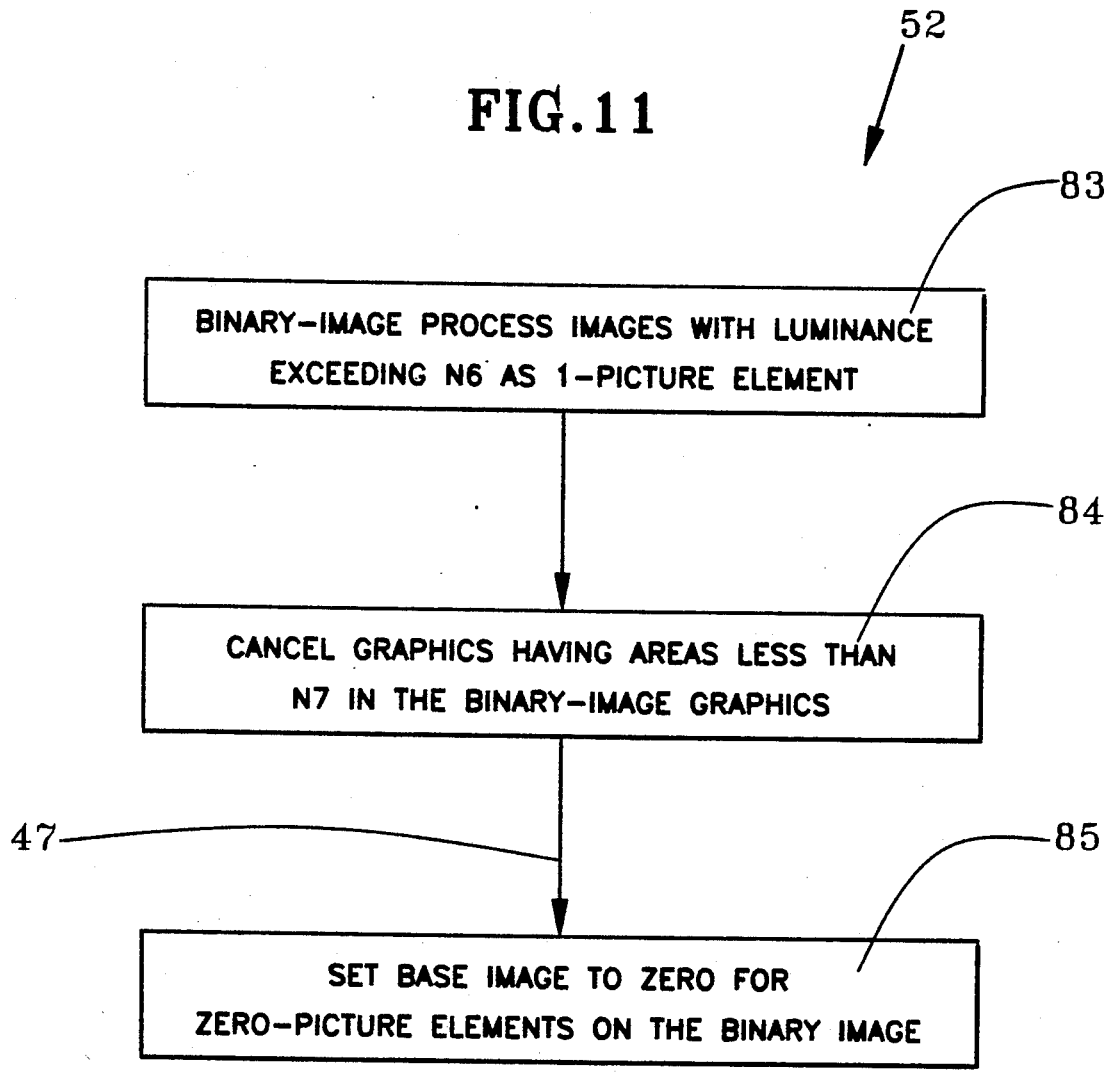
FIG. 11 is a flow chart of a particle shape-arranging program.

Referring to FIG. 11, the particle shape arrangement program 52 is comprised further of step 83 binary-image process images with luminance exceeding N6 as 1-picture element, step 84 cancel graphics having areas less than N7 in the binary-image graphics, and step 85 set base image to zero for zero-picture elements on the binary image.

Figure 12:
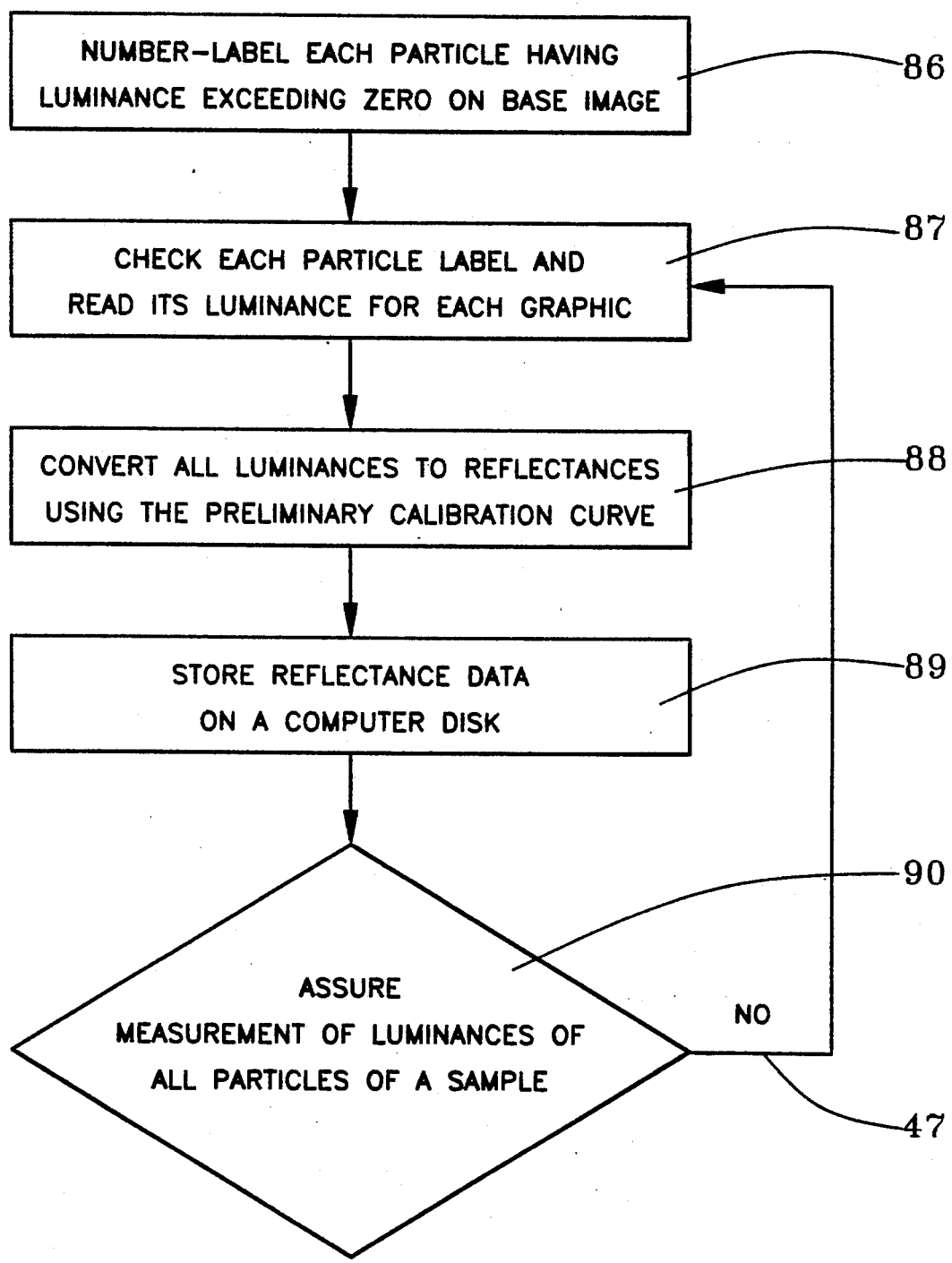
FIG. 12 is a flow chart of a luminance measuring program.

Referring to FIG. 12, the luminance-measuring program 53 is comprised further of step 86 number-label each particle having luminance exceeding zero on base image, step 87 check each particle label and read its luminance for each graphic, step 88 convert all luminances to reflectances using the preliminary calibration curve, step 89 store reflectance data on a computer disk, and step 90 assure measurement of luminances of all particles of a sample.

Figure 13:
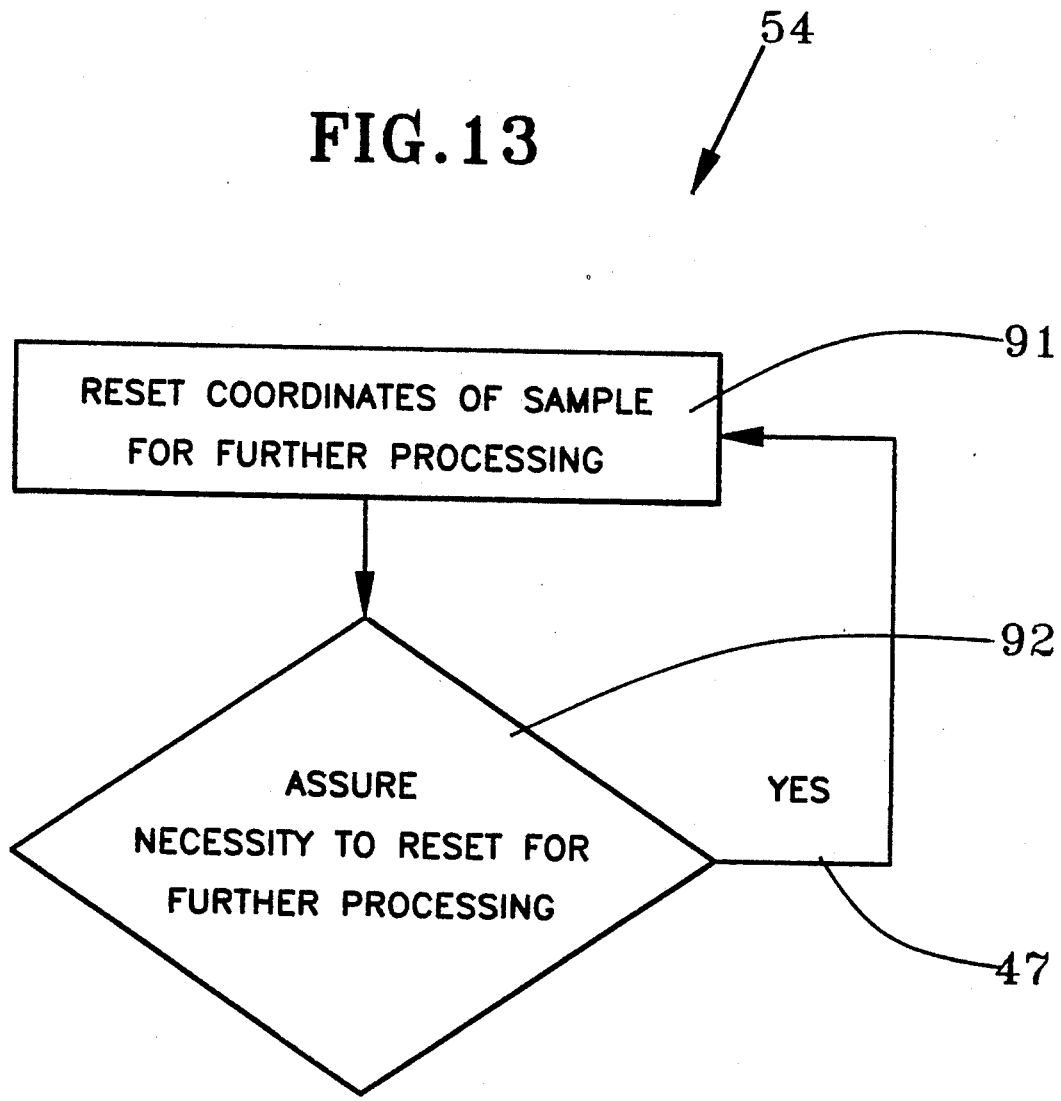
FIG. 13 a flow chart of a recycling-review program.

Referring to FIG. 13, the completion review 54 is comprised further of step 91 reset coordinates of sample for further processing, and step 92 assure necessity to reset for further processing.

A new and useful automated fossil-reflectance measurement apparatus and methods having been described, all such modifications, adaptations, substitutions of equivalents, applications and forms thereof as described by the following claims are included in this invention.

What is claimed is:

1. An automated fossil-reflectance measurement apparatus comprising:

a microscope having a sample platform automatically positional horizontal in an X-Y-coordinate plane on a fixed support;

an ore-sample tray having a bottom surface magnetically fixable on a bed of a surface grinder for grinding top surfaces of at least one ore sample in the ore-sample tray in a plane parallel to the bottom surface of the ore-sample tray;

a means for positioning the at-least-one ore sample rigidly on the ore-sample tray while a top surface of the at-least-one ore sample is being surface-ground by the surface grinder;

said sample platform having a top surface upon which the bottom surface of the ore-sample tray is fixable;

said top surface of the at-least-one ore sample being disposed in a plane parallel to the top surface of the sample platform;

an epi-prism device attached to the fixed support at a select position vertically above the sample platform;

a light source positional in light-supply relationship to the epi-prism device;

a lens extended selectively downward from the epi-prism device;

a lens barrel attached to the fixed support in remotely-focusable relationship to the lens;

an image-pickup television camera attachable to the fixed support and having remotely-focusable relationship to images communicated by way of the lens barrel;

a digital converter connected to the image-pickup television camera and connected to an image-operating processor in two-way image-transmission relationship to an image memory;

a television monitor connected to the image-operating processor by way of a television interface;

a two-way communication monitor interface connected to the digital converter and to the image-operating processor;

a two-way-communication processor interface connected to the two-way-communication monitor interface by way of a bidirectional-communication cable;

a computer mouse in selective bidirectional coordinate-control relationship to a computerized process controller;

a processor display unit connected to the computerized process controller;

a storage-medium input-output device connected to the computerized process controller;

a computer program on a computer disk having automated control of the X-Y coordinate plane;

a control-program bay in which the computer disk having automated control of the X-Y coordinate plane is insertional in the operating means in the storage-medium input-output device;

a computer operating means in the storage-medium input-output device;

a recording-program bay and operating means in the storage-medium input-output device;

process control means connected to the process controller; and an imaging input control means connected to the television interface.

2. An automated fossil-reflectance measurement apparatus according to claim 1 and further comprising:
at least one step motor in step-motor control of X-Y-coordinate positioning of the sample platform by way of appropriate electrical lines extended from the television interface to the image-pickup television camera.

3. An automated fossil-reflectance measurement apparatus according to claim 1 and further comprising:
at least one step motor in step-motor control of focussing of the image-pickup television camera by way of appropriate electrical lines extended from the television interface to the image-pickup television.

4. An automated fossil-reflectance measurement apparatus according to claim 1 wherein the imaging input control means connected to the television interface is the computer mouse.

5. An automated fossil-reflectance measurement apparatus according to claim wherein the imaging input control means connected to the television interface is a computer keyboard with directional-control key means.

6. An automated fossil-reflectance measurement apparatus according to claim 1 wherein the process control means connected to the process controller is an input computer mouse.

7. An automated fossil-reflectance measurement apparatus according to claim wherein the process control means connected to the process controller is a computer keyboard with directional-control key means.

8. An automated fossil-reflectance measurement apparatus according to claim wherein the control-program bay and operating means in the storage-medium input-output device and the recording-program bay and operating means in the storage-medium input-output device are computer-disk devices.

9. An automated fossil-reflectance measurement apparatus according to claim 1 and further comprising:
a sample tray positionable on the sample platform;
a sample bay in the sample tray sized and shaped to contain hardenable adhesive for securing at least one sample in the sample tray while a top surface of the at-least-one sample is being ground to a predetermined uniform height and then positioned on the sample platform for analysis.

10. An automated fossil-reflectance measurement apparatus according to claim 1 and further comprising:
a control program and a recording program on computer disks positional and operable in the respective control-program and recording bays to provide instructions for automatic measuring and recording of vitrinite-maceral, kerogen and other fossil reflectance of at least one sample of material on the sample platform.

11. A method for using an automated fossil-reflectance measurement apparatus comprising the steps of:
mounting a microscope with a sample platform automatically positional horizontally in an X-Y-coordinate plane on a fixed support;
magnetically fixing an ore-sampling tray having a bottom surface onto a bed of a surface grinder for grinding top surfaces of at least one ore sample in the ore-sample tray in a plane parallel to the bottom surface of the ore-sample tray;
positioning the at-least-one ore sample rigidly on the ore-sample tray while a top surface of the at-least-one ore sample is being surface-ground by the surface grinder;
fixedly securing the bottom surface of the ore-sample tray to a top surface of the sample platform;
positioning the top surface of the at-least-one ore sample in a plane parallel the top surface of the sample platform;
securing an epi-prism device to the fixed support at a select position vertically above the sample platform;
positioning a light source in light-supply relationship to the epi-prism device;
extending a lens selectively downward from the epi-prism device;
attaching a lens barrel to the fixed support in remotely-focusable relationship to the lens;
attaching an image-pickup television camera to the fixed support in remotely-focusable relationship to images communicated by way of the lens barrel;
connecting a digital converter to the image-pickup television camera and to an image-operating processor in two-way image-transmission relationship to an image memory;
connecting a television monitor to the image-operating processor by way of a television interface;
connecting a two-way communication monitor interface to the digital converter and to the image-operating processor;
connecting a two-way-communication processor interface to the two-way-communication monitor interface by way of a bidirectional-communication cable;
providing a computer mouse in selective bidirectional coordinate-control relationship to a computerized process controller;
connecting a process display unit to the computerized process controller;
connecting a storage-medium input-output device to the computerized process controller;
providing a computer program on a computer disk having automated control of the X-Y coordinate plane;
providing a control-program bay in which the computer disk having automated control of the X-Y coordinate plane is insertional in the storage-medium input-output device;
providing a computer operating means in the storage-medium input-output device;
providing a recording-program bay and operating means in the storage-medium input-output device;
connecting a process control means to the process controller;
connecting an imaging input control means to the television interface;
providing at least one step motor in step-motor control of X-Y-coordinate positioning of the sample platform by means of appropriate electrical lines extended from the television interface to the image-pickup television camera;
preparing at least one sample of fossil for reflectance measurement by positioning the at-least-one sample on the sample tray and forming a smooth, flat top surface thereof in a plane parallel tot he bottom surface of the sample tray;
positioning the sample tray containing the at-least-one sample of fossil on the sample platform of the automated microscope portion of the automated-reflectance measurement apparatus;
inserting the control-program computer disk into the control-program bay and operating means in the processing portion of the automated-reflectance measurement apparatus;

inserting the recording-program computer disk into the recording-program bay and operating means in the processing portion of the automated-reflectance measurement apparatus;

activating the automated-reflectance measurement apparatus;

activating the recording program as directed by instructions appearing on the television monitor in the input portion of the automated-reflectance measurement apparatus;

observing reflectance data of the at-least-one sample of fossil appearing on the processor display unit of the automated-reflectance measurement apparatus as desired for manual-override control while such data is being recorded on the recording-program computer disk; and removing the recording-program computer disk from the recording-program bay for future reference and optional print-out on the computer print-out apparatus.

12. A method for using an automated fossil-reflectance measurement apparatus according to claim 11 wherein step A preparation of the at-least-one sample of fossil for reflectance measurement comprises positioning the at-least-one sample of fossil in a sample bay of a sample tray having a select amount of hardenable adhesive in a bottom portion of the sample bay, allowing the hardenable adhesive to harden, positioning the sample tray containing the at-least-one sample of fossil on a grinding bed of a surface-grinder machine, and grinding all measurement-surface area of the at-least-one sample of fossil to a uniform height relative to a bottom surface of the sample tray.

13. A method for using an automated fossil-reflectance measurement apparatus according to claim 11 wherein reflectance measurement is continued for analysis of each of a plurality of samples of fossil on a sample tray in accordance with such operational instructions as may appear on the television monitor.

* * * * *